(12) United States Patent
Kidder

(10) Patent No.: US 10,993,428 B1
(45) Date of Patent: May 4, 2021

(54) SPORTMAN'S HOLDER SYSTEM WITH LEG ADAPTER

(71) Applicant: Kevin Robert Kidder, Buckeye, AZ (US)

(72) Inventor: Kevin Robert Kidder, Buckeye, AZ (US)

( * ) Notice: Subject to any disclaimer, the term of this patent is extended or adjusted under 35 U.S.C. 154(b) by 0 days.

(21) Appl. No.: 15/896,890

(22) Filed: Feb. 14, 2018

Related U.S. Application Data

(60) Provisional application No. 62/458,620, filed on Feb. 14, 2017.

(51) Int. Cl.
*A01K 97/10* (2006.01)

(52) U.S. Cl.
CPC .................. *A01K 97/10* (2013.01)

(58) Field of Classification Search
CPC ...................................... A01K 97/10
USPC .......................................... 43/21.2
See application file for complete search history.

(56) References Cited

U.S. PATENT DOCUMENTS

| | | | |
|---|---|---|---|
| 1,761,497 A * | 6/1930 | Smith | A01K 97/10 224/222 |
| 1,786,254 A | 12/1930 | Meehan | |
| 2,658,650 A | 11/1953 | Jasper | |
| 2,969,899 A * | 1/1961 | Brooks | A01K 97/10 224/581 |
| 4,802,612 A | 2/1989 | Anderson | |
| 4,817,323 A | 4/1989 | Dennis | |
| 4,858,364 A | 8/1989 | Butts | |
| 5,123,578 A * | 6/1992 | Morse | A01K 97/10 224/249 |
| 5,520,312 A | 5/1996 | Maddox | |
| 5,546,693 A | 8/1996 | Stockton | |
| 5,573,167 A * | 11/1996 | Bebb | A01K 97/10 224/200 |
| 5,738,257 A | 4/1998 | McConnell | |
| 5,855,086 A | 1/1999 | Pandeles | |

(Continued)

FOREIGN PATENT DOCUMENTS

WO    WO2015170357    11/2015

OTHER PUBLICATIONS

Shelton Products, StrikeFighter, Retrieved on Feb. 15, 2016 from www.sheltonproducts.com/handicap.html, p. 1, 3d picture down.

(Continued)

*Primary Examiner* — Claude J Brown
(74) *Attorney, Agent, or Firm* — Adam R. Stephenson, Ltd.

(57) ABSTRACT

A fishing pole holder system has a leg adapter configured to secure a pole holder to the user's upper leg. The leg adapter fits over a person's thigh and may be secured by a strap. A pole holder is attached to the leg adapter to allow individuals with only one available hand to fish. The pole holder has a recess for receiving the grip end of the fishing pole. A height extender may be coupled between the leg adapter and the pole holder to extend the pole holder up when a person is standing. A belt extension may be attached to the leg adapter and extend up to a person's waist where it may be attached to a belt to further secure the leg adapter in place. A line clip may be provided to allow the fishing line to be retained in position while the lure or bait is change or to remove a fish. The leg adapter with a base and recess also accommodates a rifle pod to enable one-armed hunting.

8 Claims, 8 Drawing Sheets

(56) References Cited

U.S. PATENT DOCUMENTS

| | | | |
|---|---|---|---|
| 5,956,883 A | 9/1999 | Krouth | |
| 6,003,746 A | 12/1999 | Richardson | |
| 6,029,872 A | 2/2000 | Ellington | |
| 6,141,898 A | 11/2000 | Shelton | |
| 6,237,821 B1 | 5/2001 | Owen | |
| 6,269,990 B1 | 8/2001 | Gray | |
| 6,357,639 B1 | 3/2002 | Williams | |
| 6,591,542 B1* | 7/2003 | Jordan | A01K 97/10 224/922 |
| 7,845,106 B2 | 12/2010 | Norman | |
| 8,181,381 B1 | 5/2012 | Kelleher | |
| 8,690,035 B2 | 4/2014 | Silverman | |
| 9,924,785 B1* | 3/2018 | Gilmore | A01K 97/08 |
| 2003/0188472 A1* | 10/2003 | Congialosi | A01K 97/01 43/21.2 |
| 2007/0234631 A1* | 10/2007 | Parkison | A01K 97/10 43/21.2 |
| 2008/0301997 A1* | 12/2008 | Tempini | A01K 97/06 43/21.2 |
| 2010/0018104 A1 | 1/2010 | Pedersen | |
| 2011/0095894 A1* | 4/2011 | Gibson | A01K 97/125 340/573.2 |
| 2011/0290845 A1 | 12/2011 | Jackson | |
| 2014/0076944 A1* | 3/2014 | Marra | A01K 97/08 224/222 |
| 2015/0296763 A1* | 10/2015 | Sanders | A01K 97/10 224/200 |
| 2019/0269119 A1* | 9/2019 | Vandamia | A01K 97/10 |

OTHER PUBLICATIONS

Fish-N-Chum #2, Fishrod/rod holder, Retrieved Feb. 15, 2016 from www.fish-n-chum.com/fish-n-chum_Bait_Casting.htm.

* cited by examiner

SPORTMAN'S HOLDER SYSTEM WITH LEG ADAPTER

RELATED APPLICATION

This nonprovisional patent application claims the benefit of U.S. Provisional Application Ser. No. 62/458,620, filed Feb. 14, 2017, which is incorporated herewith.

FIELD OF THE INVENTION

The invention relates to fishing pole holder systems having a leg adapter to allow individuals with one arm to operate a fishing pole coupled thereto.

BACKGROUND

Fishing is a past time and sport enjoyed by many but requires two hands, one to hold the fishing pole and the other to reel. In many situations, a person may only have one available hand to operate the fishing pole as they may be drinking a beverage or talking on the telephone. Individuals may also want to use both hands and may not want to set their fishing pole down, as a fish may bite at any time, and quick responsiveness to set the hook is important. In addition, some individuals with only one hand or arm are not able to fish without constant aid. The same problem occurs with hunting.

SUMMARY OF THE INVENTION

In one embodiment, the invention is directed to a fishing pole holder system having a leg adapter to allow individuals with one arm to operate a fishing pole coupled thereto. An exemplary fishing pole holder system has a leg adapter that is configured around the upper leg, wherein the leg adapter is configured over a user's thigh. An exemplary leg adapter may be curved and formed to extend around a portion of the user's thigh and a strap may extend under the leg and secure the leg adapter to the user's leg. A belt extension may be coupled to the leg adapter and extend up from the leg adapter and detachably attach to the user's belt extending around their waist. The belt extension provides additional support to prevent the leg adapter from sliding down the user's leg when the user stands or moves about. An exemplary fishing pole holder system has a pole holder having a pole receiver to receive the grip end of a fishing pole. An exemplary pole receiver has a recess, such as a cylindrical recess or cavity for receiving the grip end of a fishing pole. The grip end of the fishing pole may be inserted into the cylindrically shaped recess to secure the fishing pole to the pole receiver. An exemplary fishing pole holder system has a height extender that may be used to extend the fishing pole holder from the leg adapter. This configuration may be used when a person is standing, for example.

An exemplary leg adapter has a top surface for mounting the pole holder and an inside surface the extends over and in some cases around a portion of the user's upper leg, or thigh. A leg adapter has a length from the knee end to the extension end and a length axis that extends along the length of the leg adapter. A leg adapter may have a length of about 100 mm or more, about 150 mm or more, about 200 mm or more, about 350 mm or less, about 250 mm or less, about 200 mm or less and any range between and including the lengths provided. A leg adapter may extend only over a user's upper leg and the length may be adjusted based on the user's size. A leg adapter may have curved sides that extend down around a portion of the user upper leg. These sides provide additional stability for the leg adapter. A leg adapter may include a mount portion, or raised portion, wherein the pole holder is coupled thereto.

An exemplary belt extension may be detachably attachable to the leg adapter and may be adjustable in length from the leg adapter. An exemplary belt extension may slide along the length of the leg adapter and be attached in a desired position as required by the size of the user. A belt extension retainer may be used to secure the belt extension to the leg adapter. A belt extension may have an adjustable length of about 25 mm or more, about 50 mm or more, about 100 mm or more, about 150 mm or more and any range between and including the lengths provided. An exemplary belt extension may incorporate any suitable type of belt attachment feature including, but not limited to, a clip, an aperture for extending the belt therethrough and the like. An exemplary belt extension also provides some cushioning from the brace end of a pole holder to prevent the brace end of the pole holder from pushing on the user, especially when a height extender is used.

An exemplary fishing pole holder system has a pole receiver having a recess for receiving the grip end of a fishing pole. The pole receiver may be detached from the leg adapter or a base and may be rotatably adjustable in position. A pole receiver attachment feature may have an aperture for receiving a fastener, such as a threaded bolt, for example. A pole receiver may also have an extension that is configured for insertion into a recess to secure the pole receiver to a base. A pole receiver may have a hinge that enables a portion of the pole receiver to rotate about the hinge. When a fish bites the bait or lure, it is important to set the hook by pulling back on the fishing pole, and a rotating pole receiver portion allows this important function with the pole secured to the pole holder. A pole holder attachment may be detachably attachable to the pole holder to allow different attachments, such as to a receiver recess or to an aperture in a height extender, for example.

An exemplary fishing pole holder system utilizes a height extender that is configured to extend from the leg adapter or base to the pole holder. An exemplary height extender has a length from a base end to a pole holder end and this length may be about 100 mm or more, about 150 mm or more, about 200 mm or more, about 250 mm or more, about 300 mm or more, about 350 mm or more and any range between and including the lengths of the height extender provided. A height extender may be configured with a base end for attachment to a base or leg adapter, and a pole holder end for attachment to a pole holder. The base end may have an extension that is configured to fit within a receiver recess of a leg adapter or base. The pole holder end may be configured with an aperture for alignment with an aperture in the pole holder to receive a fastener, such as a threaded bolt to secure the two components together.

An exemplary fishing pole holder system has a base that may have one or more receiver recesses. In an exemplary embodiment, a base has a first receiver recess configured on a top surface of the base to allow attachment of a pole holder thereto. This configuration may be used when a person is sitting. A base may also have a second receiver recess configured on the knee side and configured for attachment of a height extender. When standing, a height extender may be inserted into the second receiver recess and a pole holder may be attached to the pole holder end of the height extender. A base may be configured into a leg adapter or may be a separate component that is attached or detachably attached to the leg adapter.

An exemplary fishing pole holder system has a line clip have a line retainer aperture to hold the fishing line for removal of a fish or for re-baiting, for example. An exemplary line clip is configured on the leg adapter where it is easy to manipulate. An exemplary line clip may be detachably attachable to the leg adapter and may have a magnet that couples with a magnet on the leg adapter.

In yet another embodiment, there is a rifle holder system that includes a leg adapter that extends around a portion of a person's thigh; a belt extension that extends from the leg adapter and has a belt attachment feature; and a rifle pod comprising a rifle attachment place; a telescoping rod on which the rifle attachment plate rotates; and a rod lower end that fits into a recess in a base of the leg adapter.

The summary of the invention is provided as a general introduction to some of the embodiments of the invention, and is not intended to be limiting. Additional example embodiments including variations and alternative configurations of the invention are provided herein.

BRIEF DESCRIPTION OF THE DRAWINGS

The accompanying drawings are included to provide a further understanding of the invention and are incorporated in and constitute a part of this specification, illustrate embodiments of the invention, and together with the description serve to explain the principles of the invention.

Figure 1:
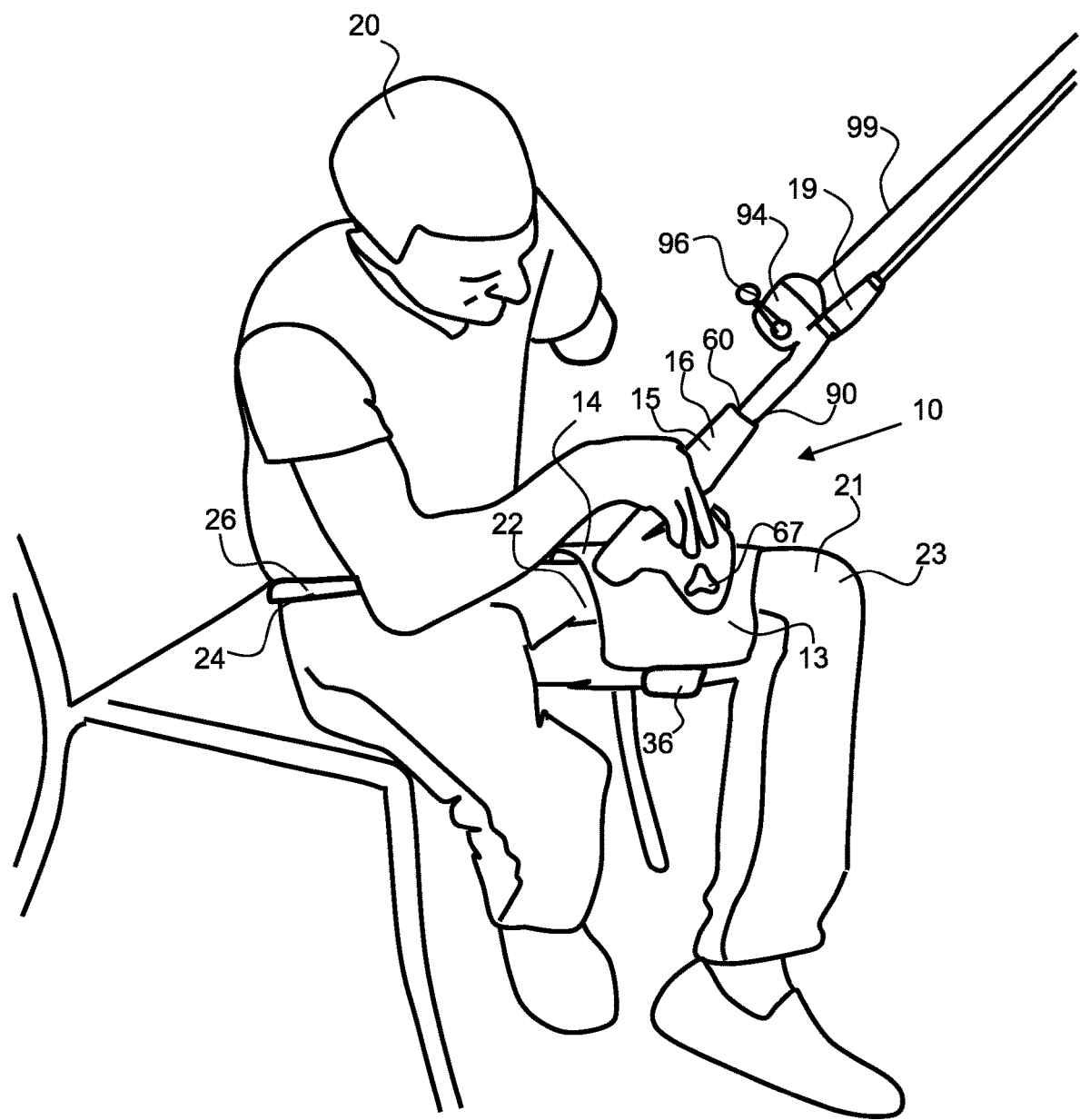
FIG. 1 shows an exemplary fishing pole holder system having a pole holder that is coupled to a leg adapter that is strapped to the user's leg.

Corresponding reference characters indicate corresponding parts throughout the several views of the figures. The figures represent an illustration of some of the embodiments of the present invention and are not to be construed as limiting the scope of the invention in any manner Further, the figures are not necessarily to scale, some features may be exaggerated to show details of particular components. Therefore, specific structural and functional details disclosed herein are not to be interpreted as limiting, but merely as a representative basis for teaching one skilled in the art to variously employ the present invention.

DETAILED DESCRIPTION

Individuals with the use of one arm are not able to fish with conventional fishing poles as it requires one hand to hold the rod, and one hand to reel the line in. In addition, fisherman often have one or both hands occupied while the fishing line is out, or when a fish bites, which requires them to drop what they are doing and grab the fishing pole and start reeling. There exists a need for a fishing pole holder system that enables a fisherman to use their hands when the line in out and to use only one hand to reel in the fish. After using the fishing system for some time, I invented a variation to accommodate hunting.

As shown in FIG. 1, an exemplary fishing pole holder system 10 has a pole holder 15 that is coupled to a leg adapter 13 that is strapped to the user's leg 21. The leg adapter is curved and extends over and around the user's thigh 22 between the waist and the user's knee 23. A strap 36 secures the leg adapter to the user's leg. A belt extension 14 extends up from the leg adapter and is attached to a belt 26 worn around the waist 24 of the user 20. The belt extension optionally provides addition support when the user stands and may prevent the leg adapter from sliding down the user's leg. The pole holder 15 is detachably attached to the leg adapter by a pole holder attachment feature 67, such as a bolt that screws into the leg adapter, or that fits through a portion of the leg adapter and into another portion of the pole holder. The pole holder has a pole receiver 16 that comprises recess 60 for receiving the grip end 90 of the fishing pole 19. The fishing pole is secured in the fishing pole holder which enables the user, having one arm, to rotate the crank 96 of the fishing reel 94 to draw in the fishing line 99 and a fish hooked thereto.

Figure 2:
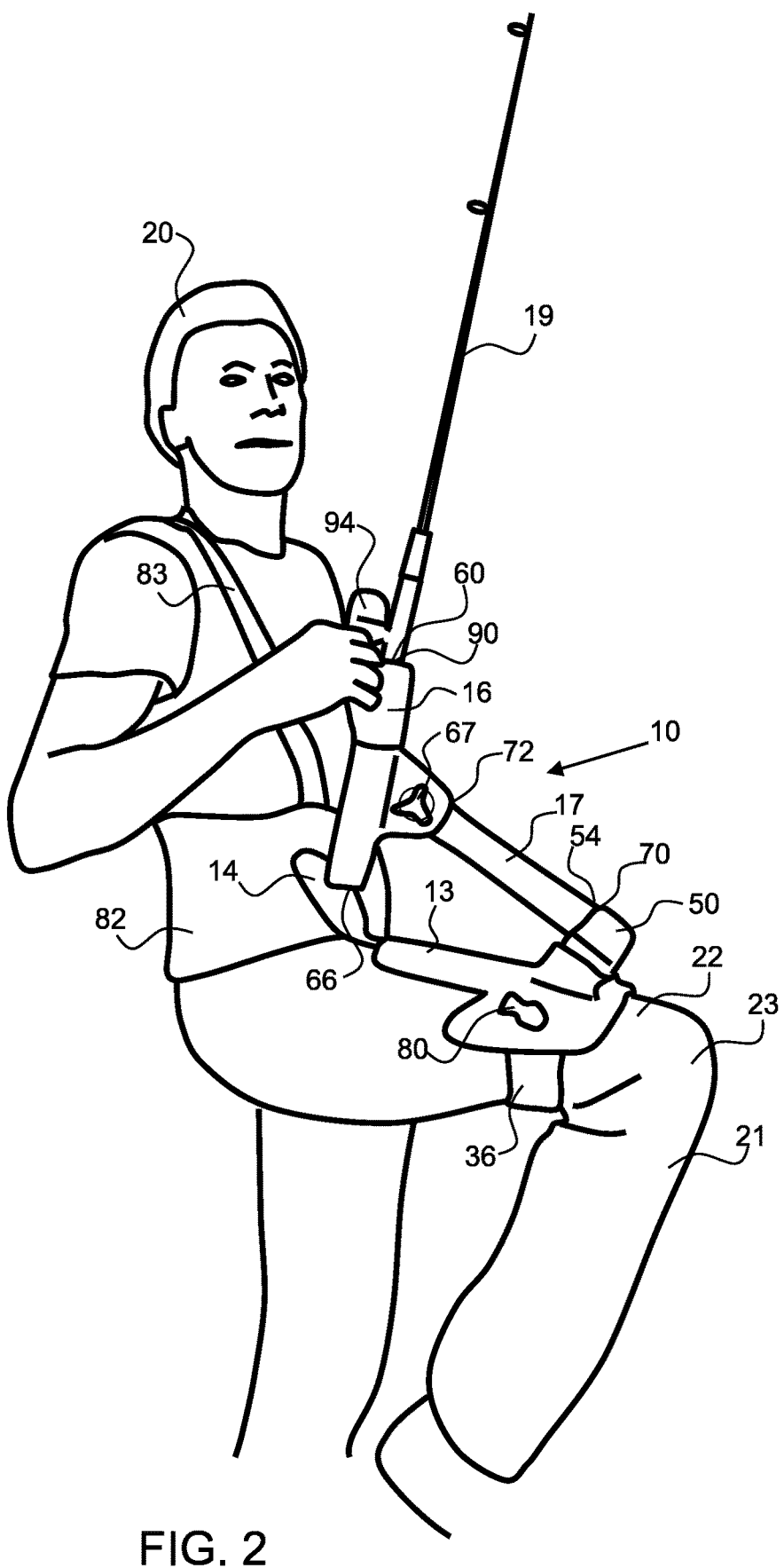
FIG. 2 shows an exemplary fishing pole holder system having a height extender coupling the pole holder to the leg adapter.

As shown in FIG. 2, an exemplary fishing pole holder system 10 has a height extender 17 that is coupling the pole holder 15 to the leg adapter 13. The height extender 17 has a pole holder end 72 and a base end 70. The pole holder end is configured to detachably attach to the pole holder by the pole holder attachment feature 67. The pole holder and the height extender may comprise apertures that can be aligned and secured together by a fastener, such as a bolt. The pole holder and/or the height extender may comprise threads on the aperture for coupling with the fastener bolt. The base end 70 of the height extender is detachably attached to the base 50. The base end may comprise an extension, such as a rod that is adapted to fit into the second receiver recess 54 of the base 50. The height extender brings the fishing pole closer to the user 20 when they are standing, as shown. A fishing pole 19 is configured in the pole holder with the grip end 90 inserted into the recess of the pole receiver 16. The crank of the reel 94 is being manipulated by the user 20. The brace end 66 of the pole holder is resting on the belt extension 14. A waist strap 82 further provide comfort to the user from the pressure exerted by the brace end. The waist strap is secured by suspenders 83, as shown. The leg adapter 13 extends along the user's thigh 22. A base 50 is secured to the leg adapter 13 and provides detachable attachment of the height extender and/or the pole holder, as described herein. A strap 36 extends around the user's leg to secure the leg adapter to the user's leg 21. A line clip 80 is coupled to the leg adapter to provide a convenient means to secure the line while attaching a new lure or attaching new bait to a hook.

Figure 3:
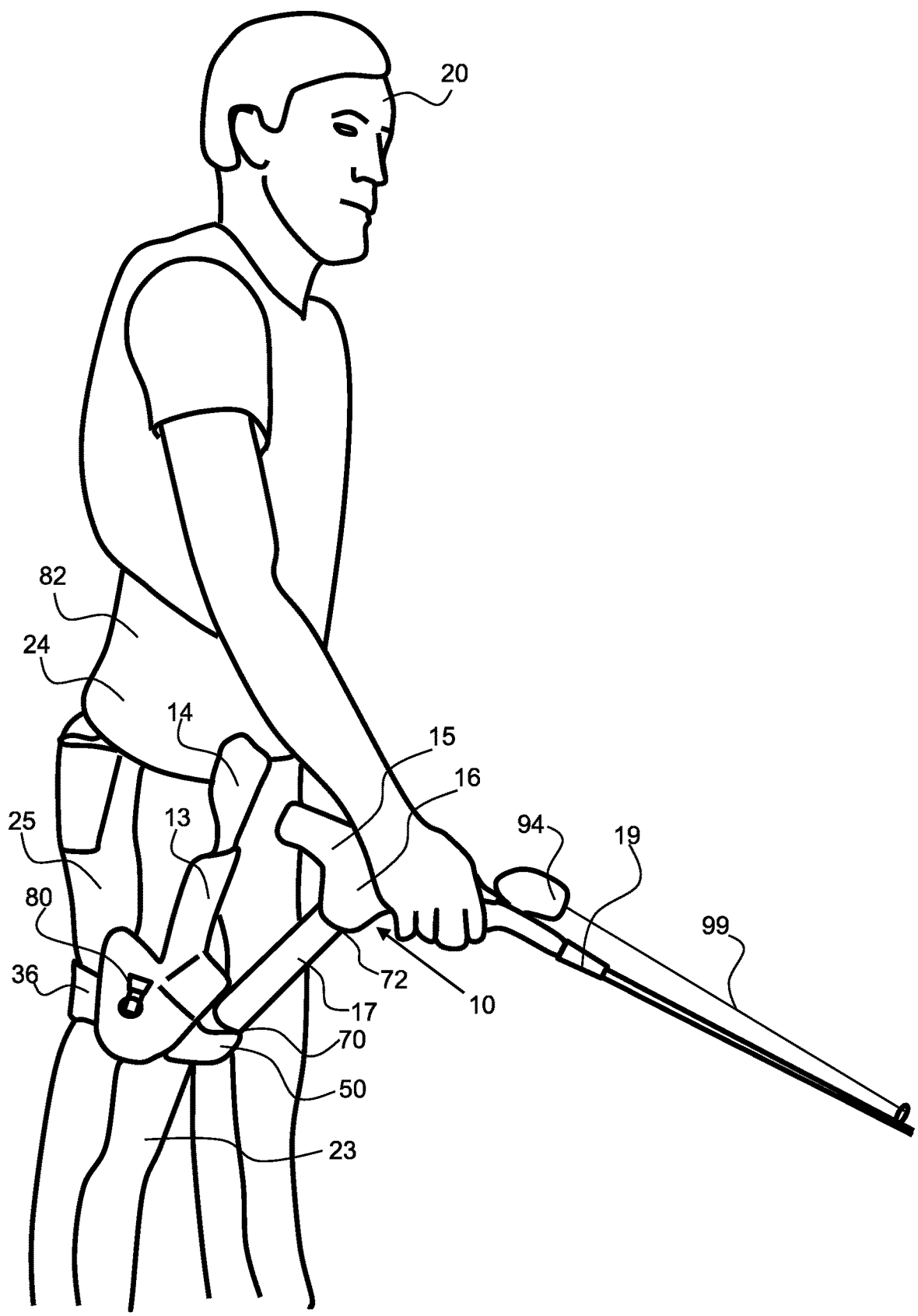
FIG. 3 shows an exemplary fishing pole holder system having a height extender coupling the pole holder to the leg adapter and the belt extension extending up to a waist strap.

As shown in FIG. 3, an exemplary fishing pole holder system 10 has a height extender 17 that is coupling the pole holder 15 to the leg adapter 13. The height extender 17 has a pole holder end 72 and a base end 70. The height extender 17 is rotated away from the user 20 as shown. The pole holder 15 may rotate about the coupling with the height extender 17 as well. The leg adapter 13 is retained on the user's upper leg 25, or the portion of the leg from the knee to the groin.

As an example of how flexible this system is, a rifle pod (not shown) can be substituted for the fishing pole holder 15 and height extender 17. Preferred is a monopod, whose base can fit into the base 50 and its recess. Rifle monopods are available from a variety of manufacturers, including but not limited to Mossy Oak, Primos, Allen, and Hunter's Specialties. These attach to rifles, swivel and telescope. Use of this example enables a hunter to stay seated within a blind.

Figure 4:
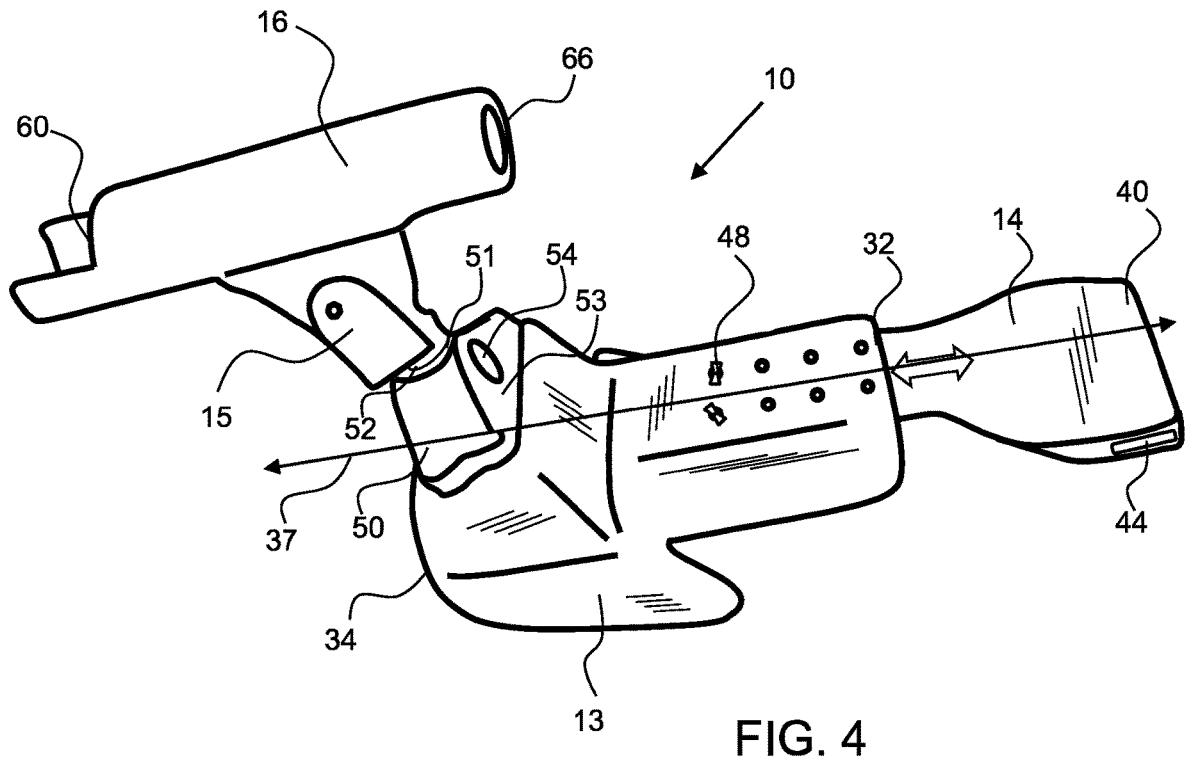
FIG. 4 shows a perspective view of an exemplary pole holder system.

As shown in FIG. 4, an exemplary pole holder system 10 comprises a leg adapter 13 with a pole holder 16 coupled thereto. A base 50 is coupled with the leg adapter 13 and comprises a first receiver recess 52 on the top 51 of the base and a second receiver recess 54 on the belt side 53 of the base. These two recesses may be configured for detachably attaching the pole holder or pole receiver and/or a height extender. The leg adapter 13 is configured to extend around a portion of a user's upper leg 25 and has a length 37 from the knee end 34 to the extension end 32. A belt extension 14 is slidably engaged with the leg adapter. The belt extension 14 can parallel a length axis of the leg adapter 13 as indicated by the double arrow 37. The belt extension 14 has a belt end 40 that is configured to be secured to a belt. This exemplary belt extension 14 comprises an aperture 44 for receiving a belt therethrough. The belt extension is secured to the leg adapter 13 by belt extension retainer 48, such as fasteners. The pole holder 15 has a pole receiver 16 portion with a pole recess 60 for receiving the grip end of a fishing pole and a brace end 66.

Figure 5:
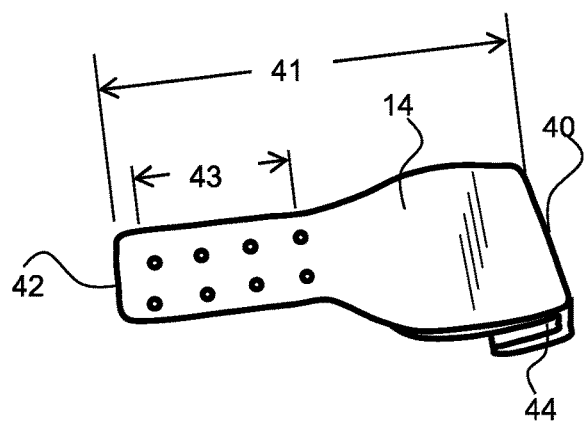
FIG. 5 shows a perspective view of an exemplary belt extension.

As shown in FIG. 5, an exemplary belt extension 14 is detached from the leg adapter and a length 41 from the adapter end 42 to the belt end 40. The belt extension 14 has a plurality of apertures for changing the length of the belt extension with respect to the leg adapter and therefore has an adjustable length 43, as shown. This exemplary belt extension 14 has a belt clip type belt attachment feature 44.

Figure 6:
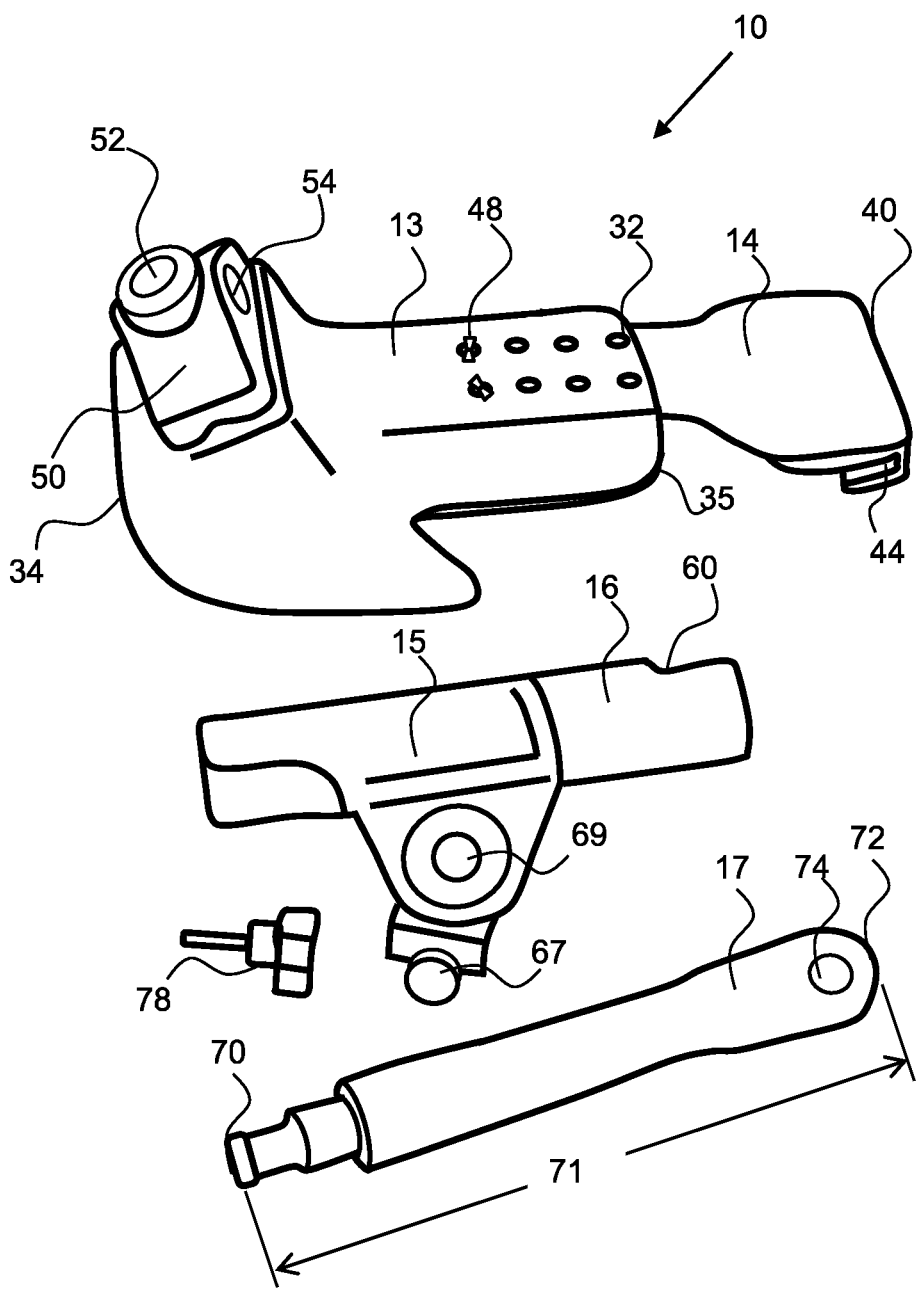
FIG. 6 show a perspective view of the components of an exemplary pole holder system.

As shown in FIG. 6, exemplary pole holder system 10 comprises a plurality of detachably attachable components. The height extender 17 is configured to attach to the first receiver recess 52 and/or the second receiver recess 54. The height extender has a length 71 from the base end 70 to the pole holder end 72. The base end 70 has an extension for insertion into one of the receiver recesses of the base 50. The pole holder end 72 has an aperture 74 for alignment with the aperture 69 of the pole holder 15 and for receiving the attachment feature 78 to secure the height extender to the pole holder. The attachment feature 78 shown is a bolt having an enlarged head to allow turning of the bolt by hand. The pole holder comprises a pole holder attachment feature 67 that is configured for attachment to the first receiver recess 52 of the base. This attachment feature 67 may be detachably attachable to the pole holder 15. For example, when the height extender is used, attachment feature 67 may be removed. The second receiver recess may be an aperture through the base 50.

Figure 7:
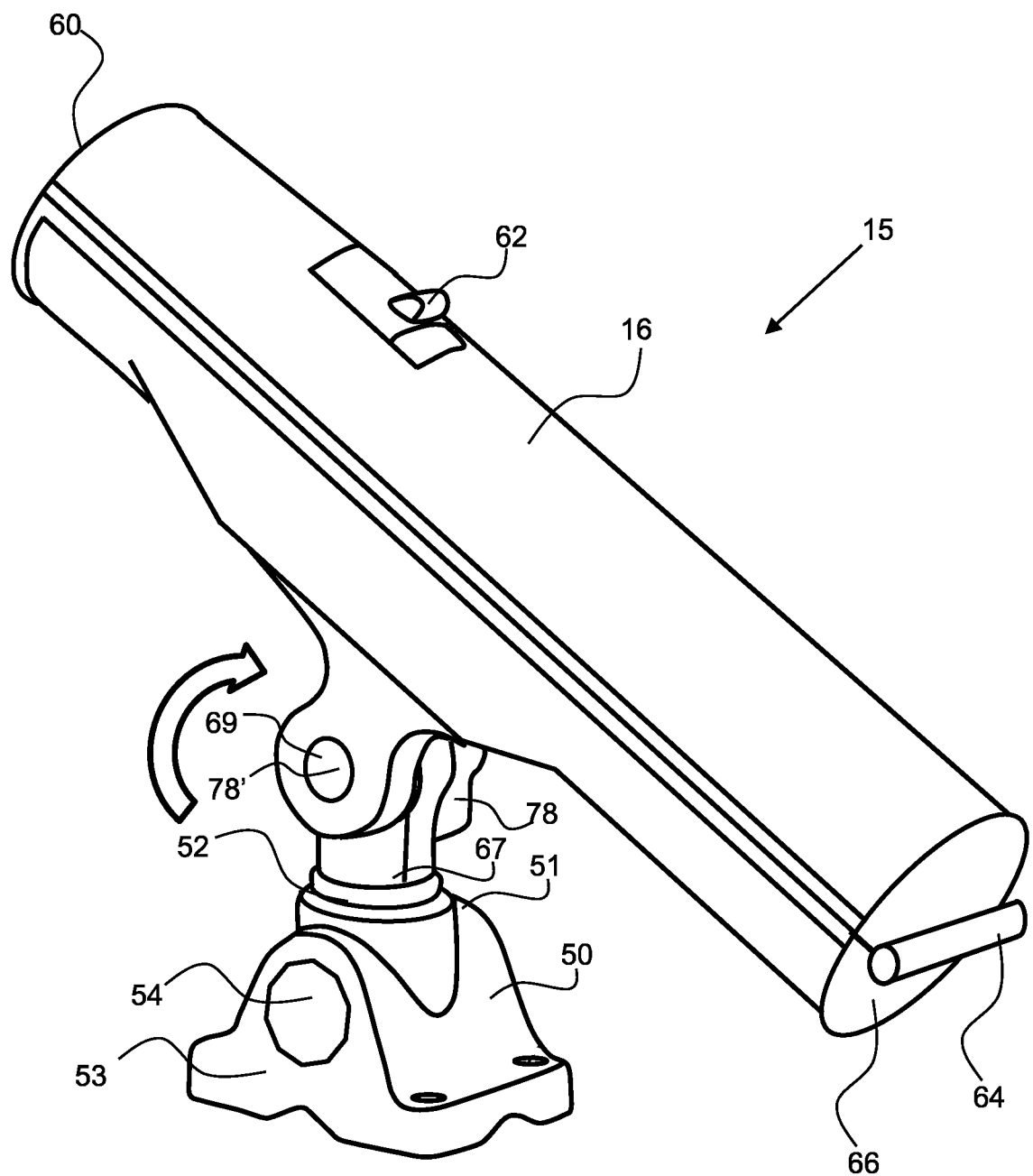
FIG. 7 shows a perspective view of an exemplary pole holder.
Figure 8:
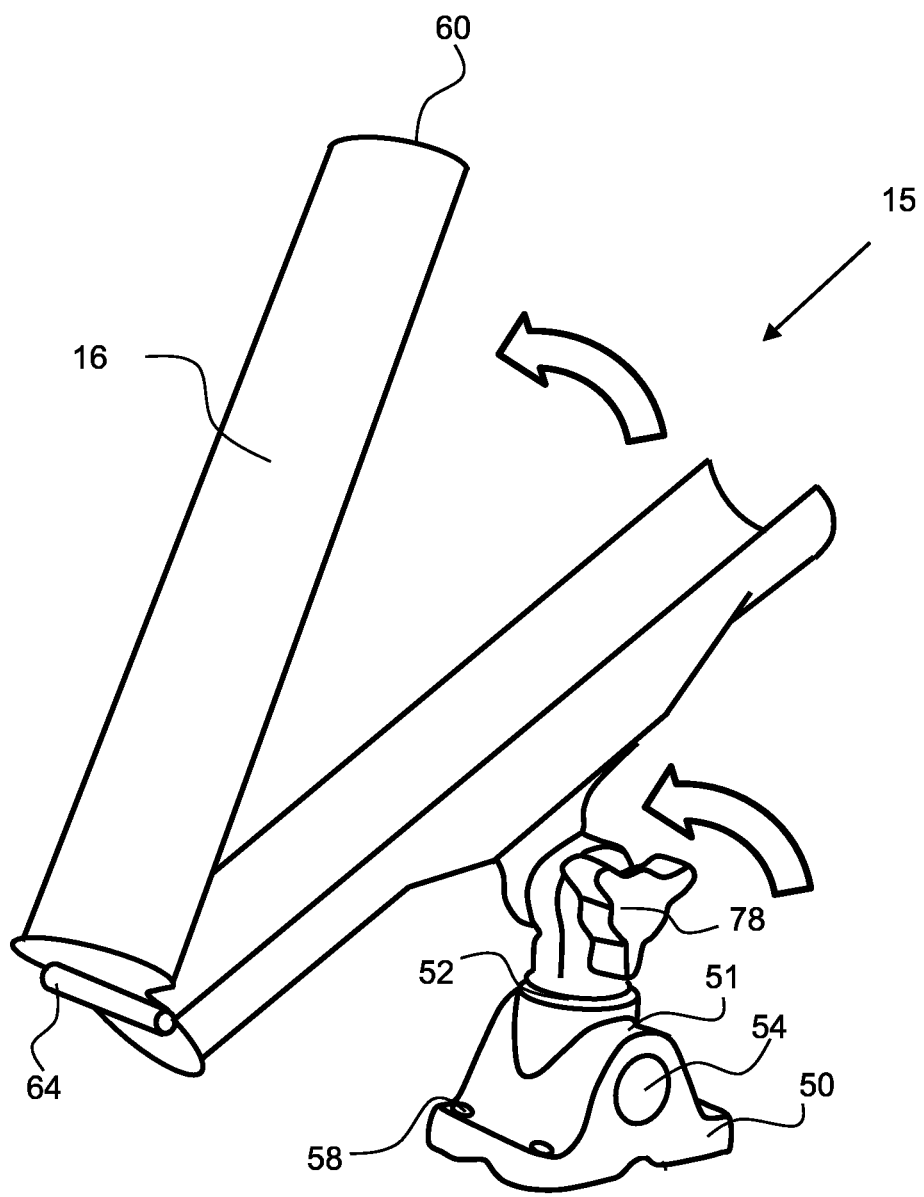
FIG. 8 shows a perspective view of an exemplary pole holder having a hinge to allow the fishing pole and a portion of the pole receiver to rotated up about the hinge.

Referring now to FIGS. 7 and 8, an exemplary pole holder 15 is attached to a base 50. The pole receiver 16 portion of the pole holder has a recess 60 for receiving a grip end of a fishing pole and an opposing brace end 66. In this embodiment, a release 62 enable a portion of the pole receiver 16 to rotate about the hinge 64, as shown in FIG. 8. This may allow a user to set the hook, when a fish is biting. The pole holder 15 is secured to the base by an extension type attachment feature 67 that is inserted into first receiver recess 52 on the top 51 of the base. The pole holder is secured in a rotational position by attachment feature 78, a threated fastener, that extends through an aperture 69 and is screwed into threads to fix the pole receiver in a desired rotational position with respect to the base 50. The second receiver recess 54 on the belt side 53 of the base, or side that faces the user or waist of the user when donned, has an irregular shape that corresponds with the insertion end of a height extender.

Figure 9:
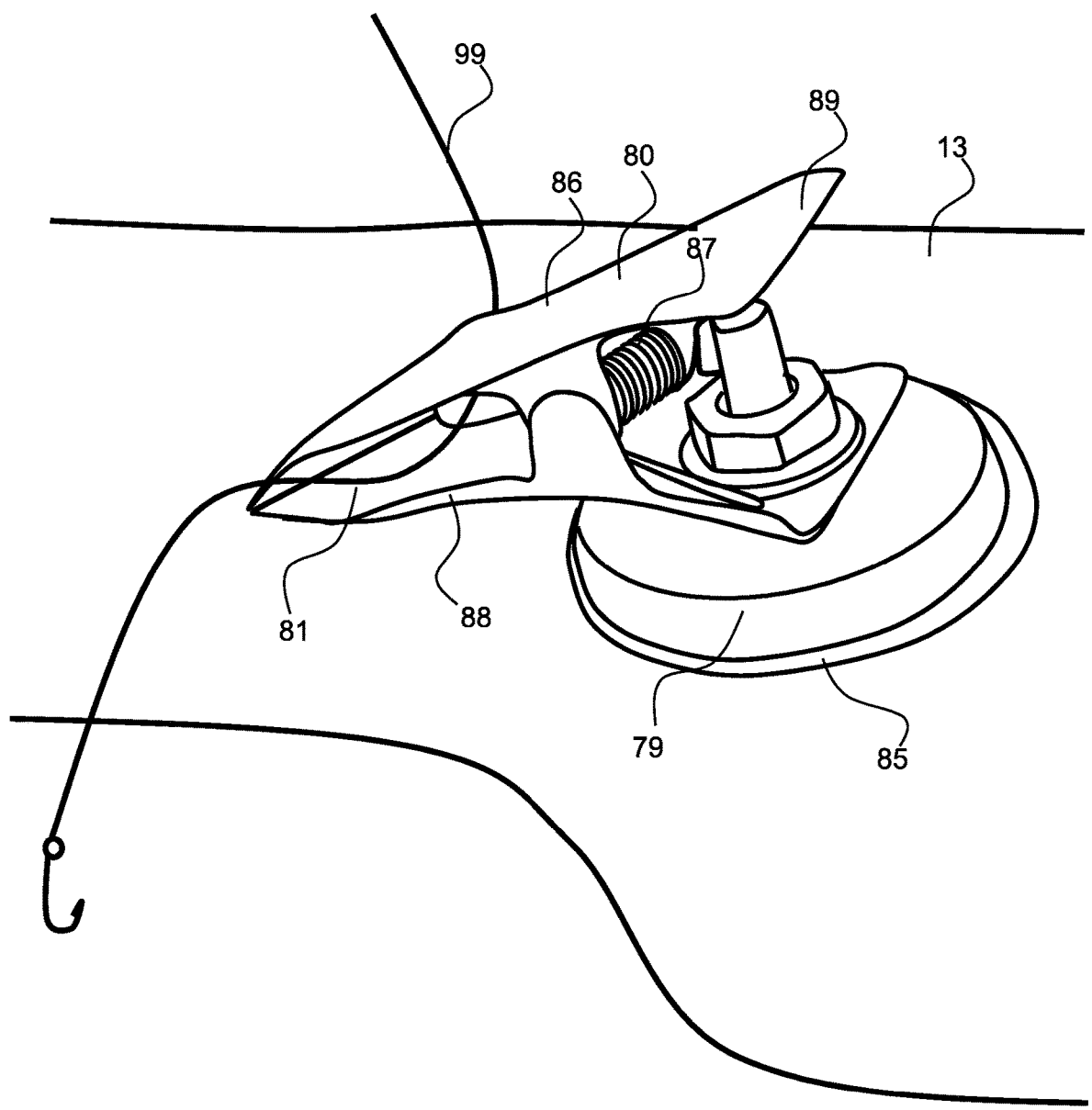
FIG. 9 shows a perspective view of an exemplary line clip.

As shown in FIG. 9, an exemplary line clip 80 has a line retainer aperture 81 between a first clip portion 86 and second clip portion 88. The first and second clip portions are coupled by a spring 87 and when the spring end 89 of the first clip portion is pressed down the line clip opens to receive the fishing line 99. The line clip is detachable attachable to the leg adapter 13 by a magnet 79 that is attracted to a magnet 85 on the leg adapter. The fishing line 99 is shown extending through the line retainer aperture 81.

It will be apparent to those skilled in the art that various modifications, combinations and variations can be made in the present invention without departing from the spirit or scope of the invention. Specific embodiments, features and elements described herein may be modified, and/or combined in any suitable manner Thus, it is intended that the present invention cover the modifications, combinations and variations of this invention provided they come within the scope of the appended claims and their equivalents.

What is claimed is:

1. A fishing pole holder system comprising:
  a) a leg adapter comprising a knee end and an extension end;
  b) a belt extension comprising a belt end and a retainer end; wherein each of the extension end of the leg adapter and the retainer end of the belt extension a plurality of apertures therethrough and the plurality of apertures configured to slidably engage the belt extension with the leg adapter through two or more fasteners, the two or more fasteners coupled through at least two of the plurality of apertures; and
  c) a base coupled with a first end of the knee end of the leg adapter, the base configured to receive a pole holder.

2. The fishing pole holder system of claim 1, wherein the belt extension comprises a loop configured to receive a belt therethrough.

3. The fishing pole holder system of claim 1, wherein the base comprises a first receiver recess for receiving the pole holder.

4. The fishing pole holder system of claim 1, further comprising a height extender comprising a base end and a pole holder end; wherein the base end of the height extender is configured to detachably attach to the base and the pole holder end is configured to attach to the pole holder.

5. The fishing pole holder system of claim 1, further comprising a line clip that is located on a first end of the support portion of the leg adapter.

6. A fishing pole holder system comprising:
  a) a leg adapter comprising a knee end and an extension end;
  b) a belt extension comprising a belt end and a retainer end wherein the belt extension is slidably coupled with the extension end of the leg adapter through two or more fasteners; and
  c) a base removably coupled to the knee end of the leg adapter, the base comprising a first receiver recess on a top side of the base configured to receive a pole holder.

7. The fishing pole holder system of claim 6, further comprising a height extender comprising a base end and a pole holder end.

8. The fishing pole holder system of claim 6, further comprising a line clip coupled to the knee end of the leg adapter.

\* \* \* \* \*